United States Patent [19]
Young et al.

[11] Patent Number: 6,028,307
[45] Date of Patent: Feb. 22, 2000

[54] DATA ACQUISITION AND REDUCTION METHOD FOR MULTI-COMPONENT FLOW

[75] Inventors: Allen R. Young, Arlington; Scot A. Johnson, College Station, both of Tex.

[73] Assignee: Computalog Research, Worth, Tex.

[21] Appl. No.: 08/939,247

[22] Filed: Sep. 28, 1997

[51] Int. Cl.$^7$ .................................................. G01V 5/12
[52] U.S. Cl. .................. 250/256; 73/152.31; 250/269.3; 702/8
[58] Field of Search .............................. 702/8; 73/152.31, 73/152.29, 152.14; 250/269.3, 256

[56] References Cited

U.S. PATENT DOCUMENTS

| | | |
|---|---|---|
| 4,441,361 | 4/1984 | Carlson et al. . |
| 4,939,362 | 7/1990 | Supernaw et al. . |
| 5,012,091 | 4/1991 | Moake . |
| 5,359,195 | 10/1994 | Gartner et al. . |
| 5,361,632 | 11/1994 | Magnani . |
| 5,375,465 | 12/1994 | Carlson ................................. 73/152.05 |
| 5,531,112 | 7/1996 | Young et al. . |
| 5,552,598 | 9/1996 | Kessler et al. . |
| 5,631,413 | 5/1997 | Young et al. . |

OTHER PUBLICATIONS

Allen R. Young, Scot A. Johnson, A New Production Logging Tool for Determining Holdups, SPE 38652.

*Primary Examiner*—Constantine Hannaher
*Attorney, Agent, or Firm*—Jack V. Musgrove; Andrew J. Dillon

[57] ABSTRACT

A method of determining a holdup value for a multiphase fluid. A first holdup component is calculated using a first detection technique which is insensitive to small inclusions of a first fluid constituent (hydrocarbons) dispersed in a second fluid constituent (water). A second holdup component is also calculated using a second detection technique which determines a percentage of the small inclusions of the first fluid constituent that are dispersed in the second fluid constituent. The first and second holdup components are then combined to yield a total holdup value. The method can further compensate for displacement of the second fluid constituent by the small inclusions of the first fluid constituent. The second holdup component is preferably calculated by inferring a maximum heavy phase density (MHPD) of the multiphase fluid.

28 Claims, 8 Drawing Sheets

```
Computalog Fluid Profile Survey
File:    F1320h.txt
Depth:   0'
Date     02 Jun 1997 13:12
BWPD=    500.0
MSCFD=    30.0

Yg FD=        0.1952
Yg FPT=       0.2980
Yg Total=     0.4350
Yg Actual=    0.4142
Yg FS Error=  0.0208
```

DATA ACQUISITION AND REDUCTION METHOD FOR MULTI-COMPONENT FLOW

BACKGROUND OF THE INVENTION

1. Field of the Invention

The present invention generally relates to oil and gas well (borehole) logging tools, and more particularly to an improved method of determining fluid holdup values by adjusting holdup measurements using complementary measurements which quantify smaller component (hydrocarbon) inclusions.

2. Description of the Related Art

In the production of underground petroleum products (oil and gas), it is important to determine the fractions of flow through a wellbore that are attributed to different components, that is, oil, water and gas. For example, it is known that water production often increases as oil reserves are depleted, or in response to a water injection program. When the degree of water present in the production flow becomes excessive, production logging surveys are used to determine the locations and rates of water entry into the flow regime. These surveys include both measurements of flow rate and attempts at determining the average density of the well fluid at various survey depths.

Various methods have been devised to calculate the fractional percentages, or "holdups," of a phase component in the fluid flow. One of the most common techniques involves the measurement of gamma ray attenuation to determine bulk density of the fluid. See, e.g., U.S. Pat. Nos. 4,939,362 and 5,012,091. In U.S. Pat. No. 5,359,195, a casing is used to shield surrounding formations from the gamma radiation so that the detector response is primarily governed by mixed phase fluids flowing in the well. In another technique described in U.S. Pat. No. 4,441,361, the multiphase fluid is blended into a mixture and directed past a rotor assembly to measure the flow rate; gamma ray attenuation is also measured to determine average density, and this information is used along with derived data for densities of individual phases to determine volumetric fractions of the fluid phases as related to the total flow regime.

There are many limitations to the use of gamma rays in determining fluid holdups. Consequently, this technique is often combined with other techniques, such as gradiomanometry (measuring differential pressure) and water-holdup measurements using capacitive or dielectric tools. For example, U.S. Pat. No. 5,361,632 teaches the use of a temperature compensated gradiomanometer to measure average fluid density, and gamma ray attenuation to calculate holdup fractions of the fluid; the flow rates for individual phases are determined using a flowmeter, and multiplying each holdup fraction by the total flow rate.

One problem that arises in measuring fluid holdups occurs when the water holdup becomes so high that the water phase becomes essentially continuous. In this case, such as a flow of a mixture of oil or gas and water with the oil or gas dispersed as bubbles in a continuous water medium, the high conductivity of the water masks varying dielectric effects that are attributable to the changes in the volumetric fraction of the oil or gas included within the mixture.

Another problem occurs in that only the dielectric constant of the central portion of the well is measured. Very often flow will vary across a section of the well, especially in highly deviated or horizontal wells, where the fluid flow may become stratified across a cross-sectional area of the borehole. This flow pattern may result in prior art fluid holdup tools detecting only a small portion of the stratified flow, such as only in one phase, and not the other portions of the flow of produced fluids. Further, different flow patterns may be present both in vertical flow and horizontal flow. In horizontal flow, bubble flow and elongated bubble flow often will occur. Additionally, stratified flow, wave flow, slug flow, annular and annular mist flow, and dispersed froth flow may occur for horizontal flow depending upon different flow parameters and flow velocities. Vertical flow patterns may also include bubble flow, froth flow, annular and annular mist flow, and slug flow. Furthermore, different densities, frictional parameters, and different phases for different constituents of segregated multiphase fluid flow result in different flow rates for the different constituents. For example, in a segregated multiphase flow in a producing well having flow constituents which consist of oil, gas and water, the gas phase may flow faster than the oil phase, which may flow faster than a water phase. In fact, in some sections of wells having multiple production zones, one phase may flow in an opposite direction within the well to that of a new flow of fluids.

Some attempts have been made to overcome the limitations of prior art methods that rely solely upon center-sampling holdup measurements, such as by utilizing a combination of center sample and fullbore gas holdup measurements. As discussed in U.S. Pat. No. 5,552,598, the downhole flow regime in a horizontal well borehole (i.e., annular or stratified flow) is determined based on a first gas holdup value measured with a fluid density tool and a second gas holdup value measured with a fullbore gas holdup tool. A different approach is disclosed in U.S. Pat. No. 5,531,112, which determines fluid holdups using a production logging tool that measures the velocity profile of multiphase fluid flow within a cross-section of a well. The tool has rotating arms with flow sensors at the tips to measure flow at different localized regions, which allows detection of variations in fluid properties attributable to flow constituents. The result is more accurate determination of holdup values. See also U.S. Pat. No. 5,631,413 which discloses a similar holdup tool and flow meter.

The foregoing techniques still suffer certain limitations. In particular, measurements of conductivity made with the sampling technique of the '598 and '413 patents are deficient in their ability to accurately measure certain water/hydrocarbon holdups. This deficiency arises because fluids that are sheared to dimensions smaller than the sensor probe tips will not be measured by the device. In other words, the probe tips tend to retain a water film when traversing these small hydrocarbon inclusions. Thus, droplets or bubbles whose diameters are smaller than that of the probe tip, e.g., 1.02 mm (0.04"), are typically not detected. In fact, inclusions must probably have a diameter of 1.27 (0.05") or larger to be seen by the probes. This problem is especially prevalent with oil/water measurements wherein the water is relatively clean and the oil is heavy, and when high multi-component flow velocities yield more finely subdivided flow geometries. It would, therefore, be desirable to devise an improved method of measuring fluid holdups in a well borehole that compensated for small, non-detectable inclusions. It would be further advantageous if the method did not require new instrumentation, but rather relied on conventional measurements, so as to avoid adding extra complexity and expense to the borehole equipment.

SUMMARY OF THE INVENTION

It is therefore one object of the present invention to provide a production logging tool for measuring fluid holdups in a well borehole.

It is another object of the present invention to provide such a tool which compensates for small hydrocarbon inclusions which might be otherwise undetectable by the tool instrumentation.

It is yet another object of the present invention to provide an improved method of reducing logged data to allow such compensation for small hydrocarbon inclusions without requiring unconventional instrumentation.

The foregoing objects are achieved in a method of determining a holdup value for a multiphase fluid, generally comprising the steps of calculating a first holdup component using a first detection technique which is insensitive to small inclusions of a first fluid constituent of the multiphase fluid dispersed in a second fluid constituent of the multiphase fluid, calculating a second holdup component using a second detection technique which determines a percentage of the small inclusions of the first fluid constituent that are dispersed in the second fluid constituent, and combining the first and second holdup components to yield a total holdup value. The first holdup component can be calculated based on data acquired by a fluid holdup tool having means for measuring flow rates of the multiphase fluid, and the second holdup component can be calculated based on data acquired by a density tool that measures the density of the multiphase fluid, based on gamma ray attenuation. The method preferably compensates for an error in the first holdup component associated with displacement of the second fluid constituent by the small inclusions of the first fluid constituent.

The second holdup component is preferably calculated by inferring a maximum heavy phase density (MHPD) of the multiphase fluid, which further involves identifying the lowest valid count rate of the gamma rays, identifying a heavy component count rate peak, and then determining a center count rate for the MHPD by moving a selected number of standard deviations of the heavy component count rate peak upward from the lowest valid count rate. The number of standard deviations can be selected using a linear regression. The system may further be devised to allow interactive selection of the number of standard deviations during density measurement. The method can be implemented in a well borehole with the tools mounted on a tool string, or in other constructions such as a pipeline used for custody transfer.

The above as well as additional objectives, features, and advantages of the present invention will become apparent in the following detailed written description.

BRIEF DESCRIPTION OF THE DRAWINGS

The novel features believed characteristic of the invention are set forth in the appended claims. The invention itself, however, as well as a preferred mode of use, further objectives, and advantages thereof, will best be understood by reference to the following detailed description of an illustrative embodiment when read in conjunction with the accompanying drawings, wherein:

DESCRIPTION OF THE PREFERRED EMBODIMENT

Figure 1:
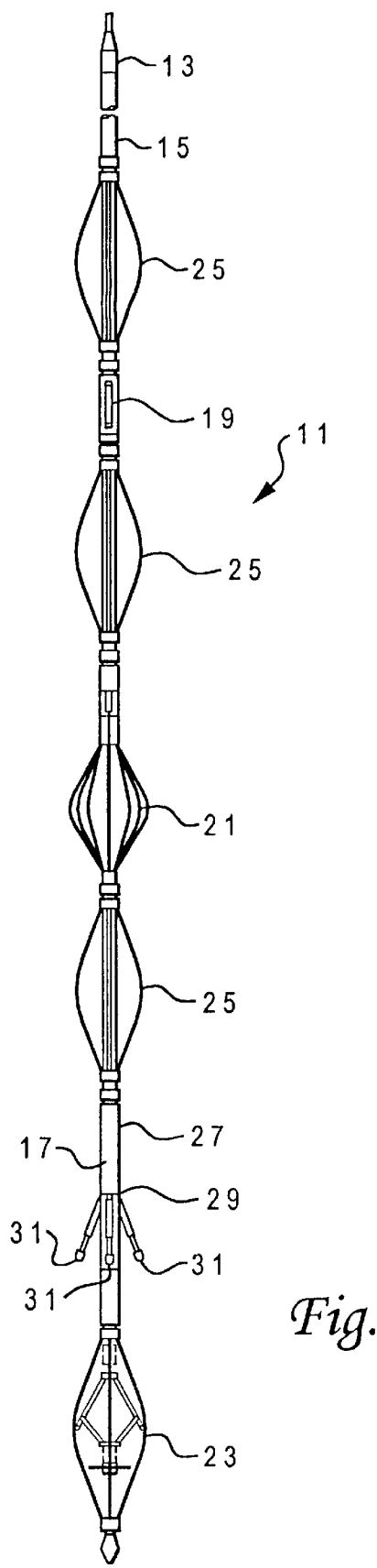
FIG. 1 is an elevational view of one embodiment of a production logging tool string used in accordance with the present invention.

With reference now to the figures, and in particular with reference to FIG. 1, there is depicted one embodiment of a production logging tool string 11 used in accordance with the present invention. Tool string 11 is used for making initial fluid holdup measurements and radioactive fluid density measurements which are used to complement the initial holdup measurements. As discussed further below, tool string 11 may be generally conventional, but novel data acquisition and reduction algorithms are presented which provide for improved measurements in multi-component flow. Of course, new tool strings may also be adapted to operate with the new data acquisition and reduction algorithms of the present invention.

Tool string 11 is essentially that described in U.S. Pat. No. 5,531,112, which is hereby incorporated, and includes a cable head 13, telemetry section 15, fluid holdup tool 17, density tool 19, deflector flowmeter 21, and full bore flowmeter 23. Bow spring centralizers 25 are included along tool string 11 for centering tool string 11 within a well.

Fluid holdup tool 17 includes an upper section 27 and a lower section 29. Three caliper arms 31 radially extend from lower section 29 of fluid holdup tool 17. Each arm 31 has mounted at its tip a flow sensor (electrical conductivity, thermal conductivity, or acoustic). The arms rotate about the axis of tool string 11, at varying angles or distances. The sensors are synchronized with control electronics to measure fluid flow at different localized regions, allowing detection of variations in fluid properties attributable to flow constituents. See the '112 patent for further details. An appropriate fluid holdup tool is available from Computalog Research, Inc. (assignee of the present invention), referred to as the Fluid Profiling Tool (FPT). The FPT is compatible with the FlexStak multiplexing scheme (FlexStak is a trademark of Computalog). A personal computer or similar device may be used for data acquisition and reduction. Tool control can be provided by the same computer or using a different microprocessor unit.

Figure 2:
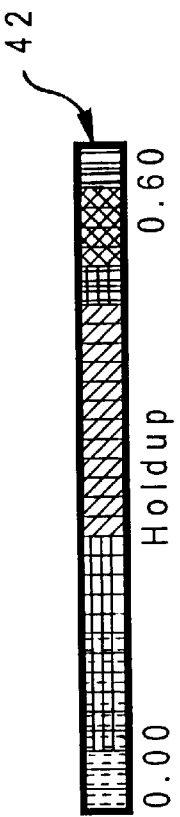
FIG. 2 is a polar plot of values used to calculate an initial fluid holdup value according to the present invention.
Figure 2:
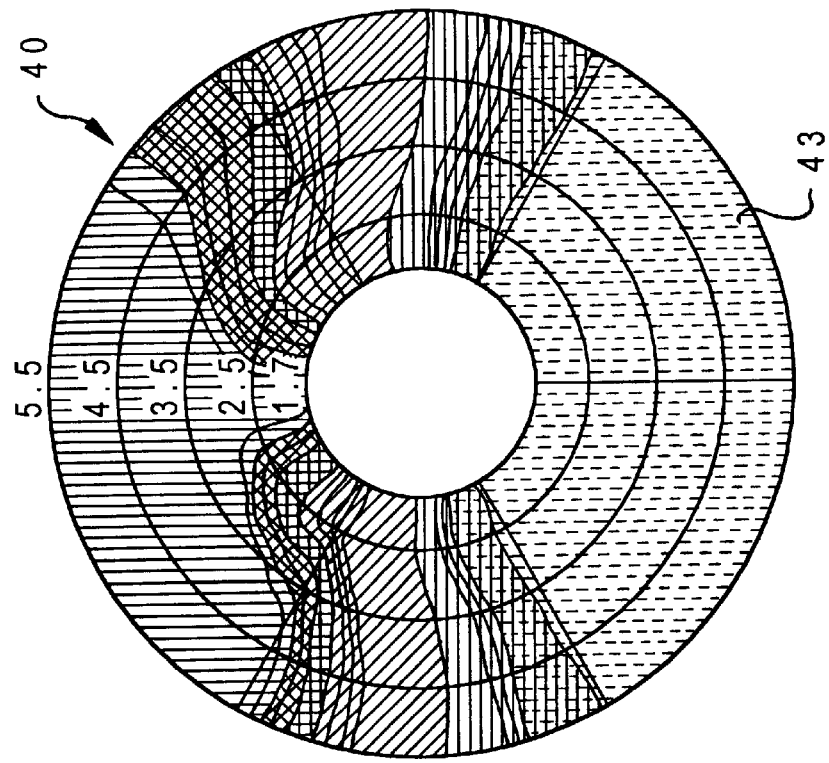

The data acquired by fluid holdup tool 17 at multiple polar angles and radii can be reduced to a plot 40 similar to that shown in FIG. 2. Arms 31 can be moved using an automated routine which eases the data gathering task. If denser sampling is required, as when precisely locating a stratified flow boundary, a manual routine can be provided. A hydrocarbon scaling bar 42 can also be included to provide a visual indication of holdup values. The holdup values at each point in plot 40 represents the duty cycle of detected conductive/ nonconductive fluids. The sensors have a near-binary response, and largely alternate between two specific output levels as water and hydrocarbon mixtures pass over them. A 50% duty cycle at the hydrocarbon (gas or oil) output level would represent a hydrocarbon holdup value of 0.5. The holdup of any fluid thus has a continuous possible range of 0 to 1.0, and simply represents the volumetric percentage of the fluid. The initial holdup value for the fluid (at the particular depth/location) is computed by multiplying the percentage area of a given individual track/sector segment 43 (relative to the total area in plot 40) with the mean holdup value for that segment, and then summing the results for all segments. This initial holdup value, referred to herein as $Y_{h\_FPT}$, is one component of the actual, total holdup, referred to herein as $Y_{h\_total}$.

One parameter that affects the value of $Y_{h\_FPT}$ is the choice of a hydrocarbon threshold. This threshold is the value used to determine whether a transition has occurred from water to hydrocarbon (and thus the binary state of the output of the sensors). The threshold yielding the best response was empirically found to be about 90% of the water/hydrocarbon span (the frequency range between the water and hydrocarbon indications). For example, if the input frequency of the sensors for water indication is 30 kHz, and the gas indication input frequency is 17 kHz, then the hydrocarbon threshold used is about 28.7 kHz.

The other component of $Y_{h\_total}$ is derived from density tool 19, and is referred to herein as $Y_{h\_FD}$. Density tool 19 is preferably a radioactive (gamma—gamma) tool having conventional components. A suitable density tool is available from Computalog, referred to as the FlexStak Radioactive Fluid Density (RFD) tool. While prior art tools use density measurements in a complementary fashion, those methods simply use counts to determine average downhole densities, and a nonlinear mapping or correction function then maps the measured density into a holdup value. In contrast, the present invention uses the count information to calculate the holdup contribution from the density measurement ($Y_{h\_FD}$) by inferring a maximum heavy-phase density (MHPD). The MHPD is determined by generating a histogram of brief (e.g., 100 millisecond) samples continuously returned by density tool 19, and searching for the lowest valid instantaneous count rate acquired during the period. The count rate is "valid" if it has a nonzero occurrence value and is contiguous with the heavy phase peak (i.e., there is no intervening count rate that has a nonzero occurrence value). When this low end is found and validated, an algorithm (discussed further below) is used to establish the center of the count rate for the MHPD. Once the center of the count rate for the MHPD is known, it is converted using calibration into the MHPD value, e.g., in grams per cubic centimeter (gram/cm$^3$). In the case of a gas/water mixture, the MHPD is nearly equal to $Y_{h\_PFD}$. Since the density of water is one gram per cubic centimeter, the numeric value of the density measurement (which is also in grams per cubic centimeter) corresponds to the holdup percentage.

The MHPD is based on the notion that particles of hydrocarbons finely dispersed in the water component will have lifetimes that far exceed the transit time required to pass through an instrument measuring volume. The use of MHPD is an acknowledgement that pure water does not exist in downhole flowing conditions, and usually has some entrained particles in it. The MHPD is therefore used to determine the level of small hydrocarbon particles dispersed in the heavy component of the flow. This principle could also be applied to a rock matrix, rather than a fluid, where the local rock composition is changing with respect to depth; the method could be used to infer the maximum formation density of the global rock matrix into which lower density inclusions are dispersed (the reverse of this method could be used if the inclusions were of higher density than the matrix).

The center of the count rate for the MHPD is determined by moving some number of standard deviations (of the heavy component peak) to the right of, or upwards from, the lowest valid count rate. For Poisson distributed counting statistics, a level of three standard deviations ($3\sigma$) is generally optimum. For flows other than single phase, sigma levels of $3.0\sigma$–$4.0\sigma$ are generally most accurate. The MHPD may be determined iteratively using an arbitrary seed number, guessing what the lowest expected count should be, and incrementing the number by a small amount if the lowest expected count deviates from the actual lowest count by more than some predetermined value. For multicomponent flow there is an apparent blurring of the statistical peak, perhaps due in part to the statistical behavior of the finely dispersed hydrocarbon inclusions. More significantly, though, very low gas flows at near horizontal inclination represent the boundary of acceptable performance for these algorithms. Because of stratification in such flows, the centralized density tool 19 becomes less effective in determining the correct MHPD. Some finely dispersed hydrocarbons may be buoyed slightly above the centerline, causing density measurements to underestimate the dispersed hydrocarbon holdup. The following discussion explains how to deal with this boundary and how to determine the appropriate sigma level.

Figure 3:
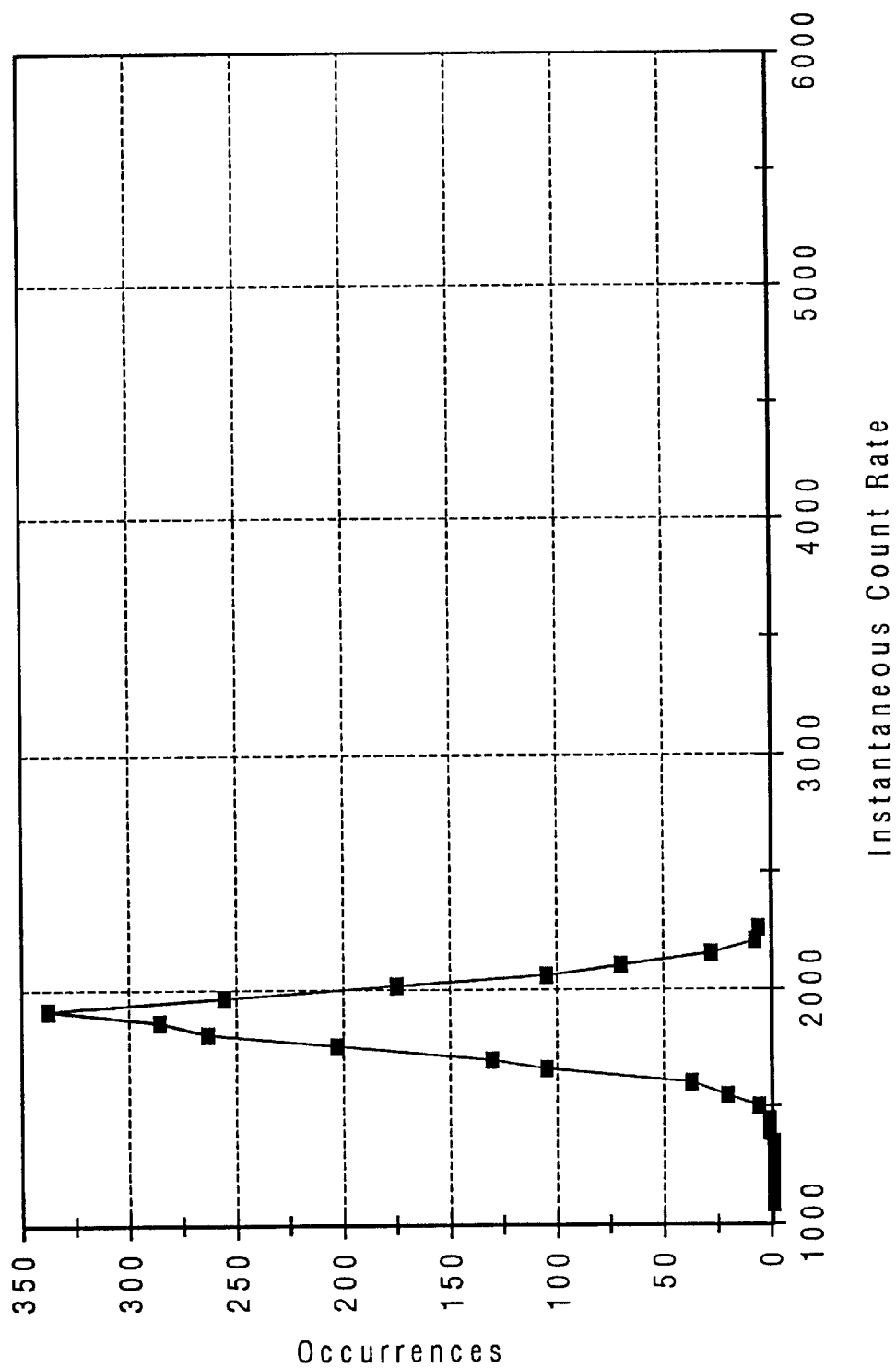
FIG. 3 is a histogram showing count rates detected with a density tool for single component water.
Figure 4:
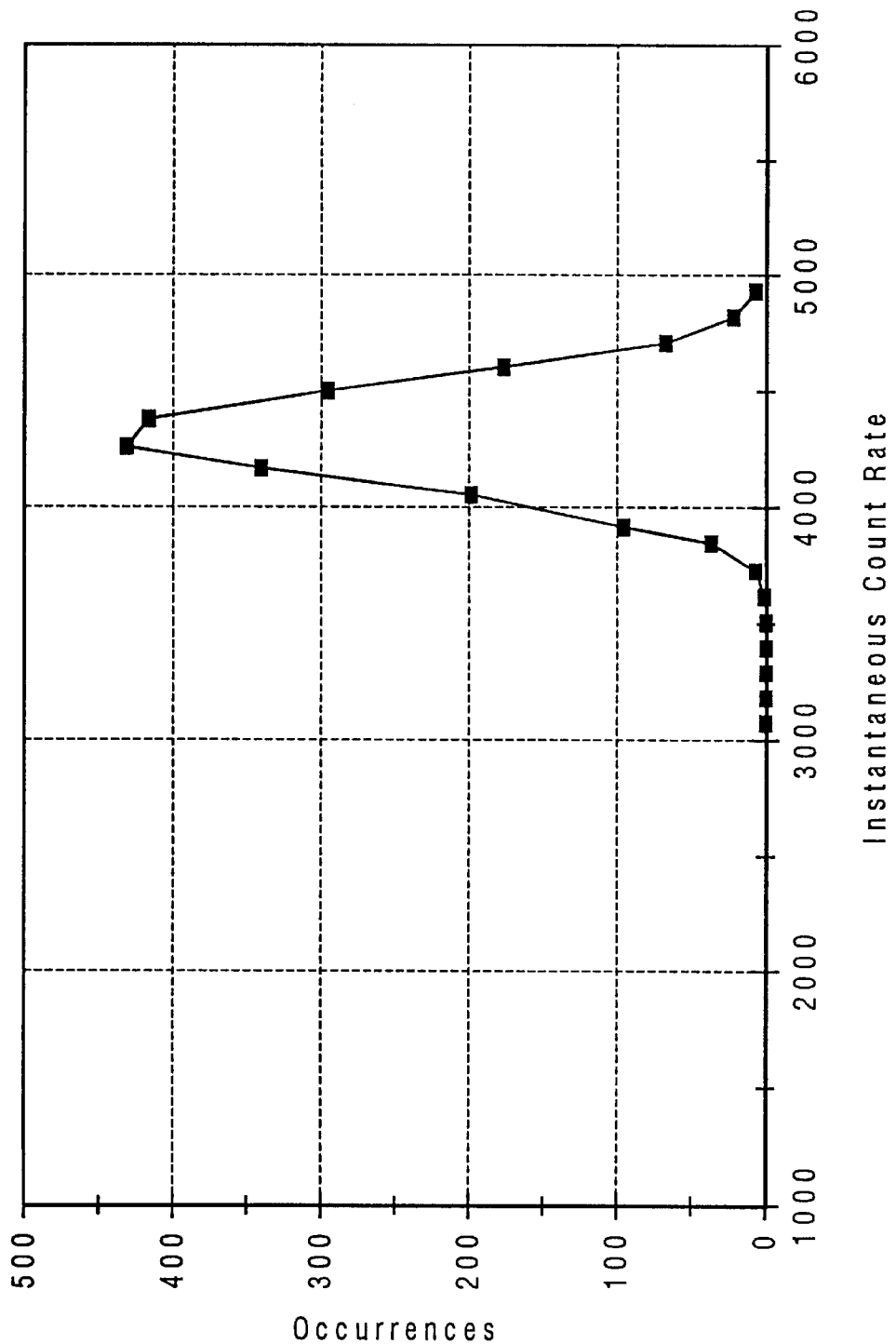
FIG. 4 is a histogram showing count rates detected with a density tool for single component air.
Figure 5:
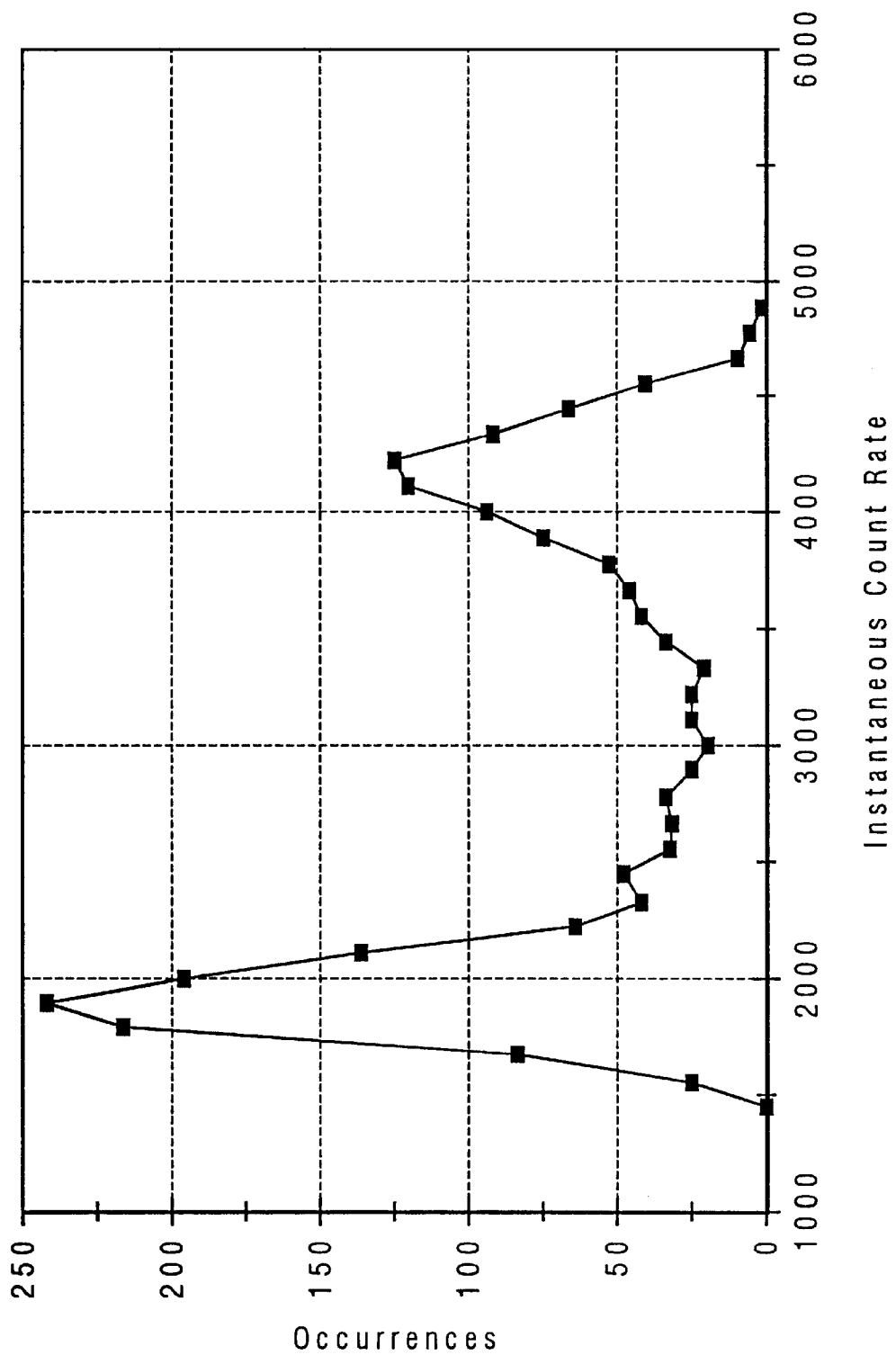
FIG. 5 is a histogram showing count rates detected with a density tool for a mixture with high water flow and low gas flow.
Figure 6:
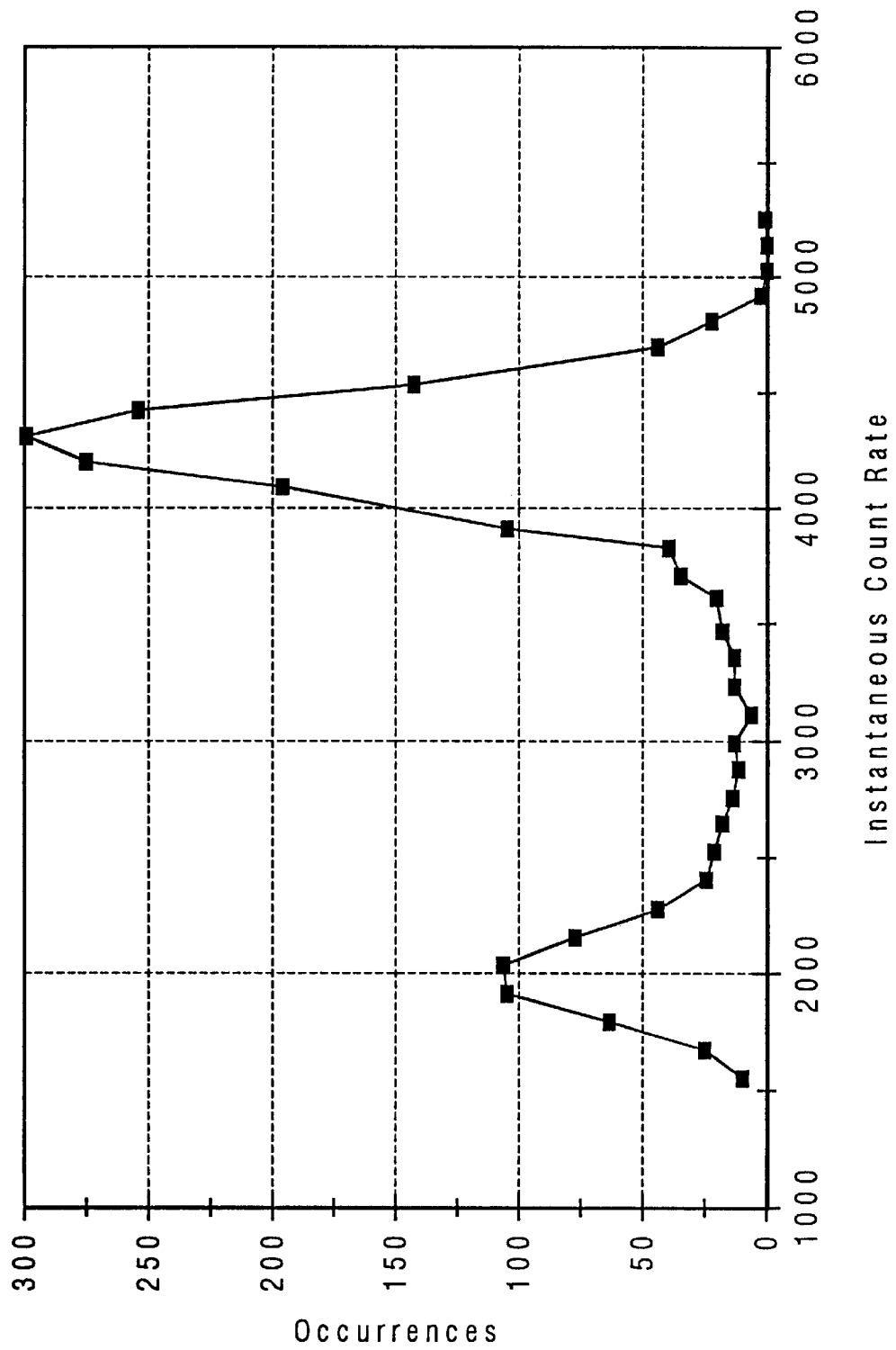
FIG. 6 is a histogram showing count rates detected with a density tool for a mixture with low water flow and high gas flow.
Figure 7:
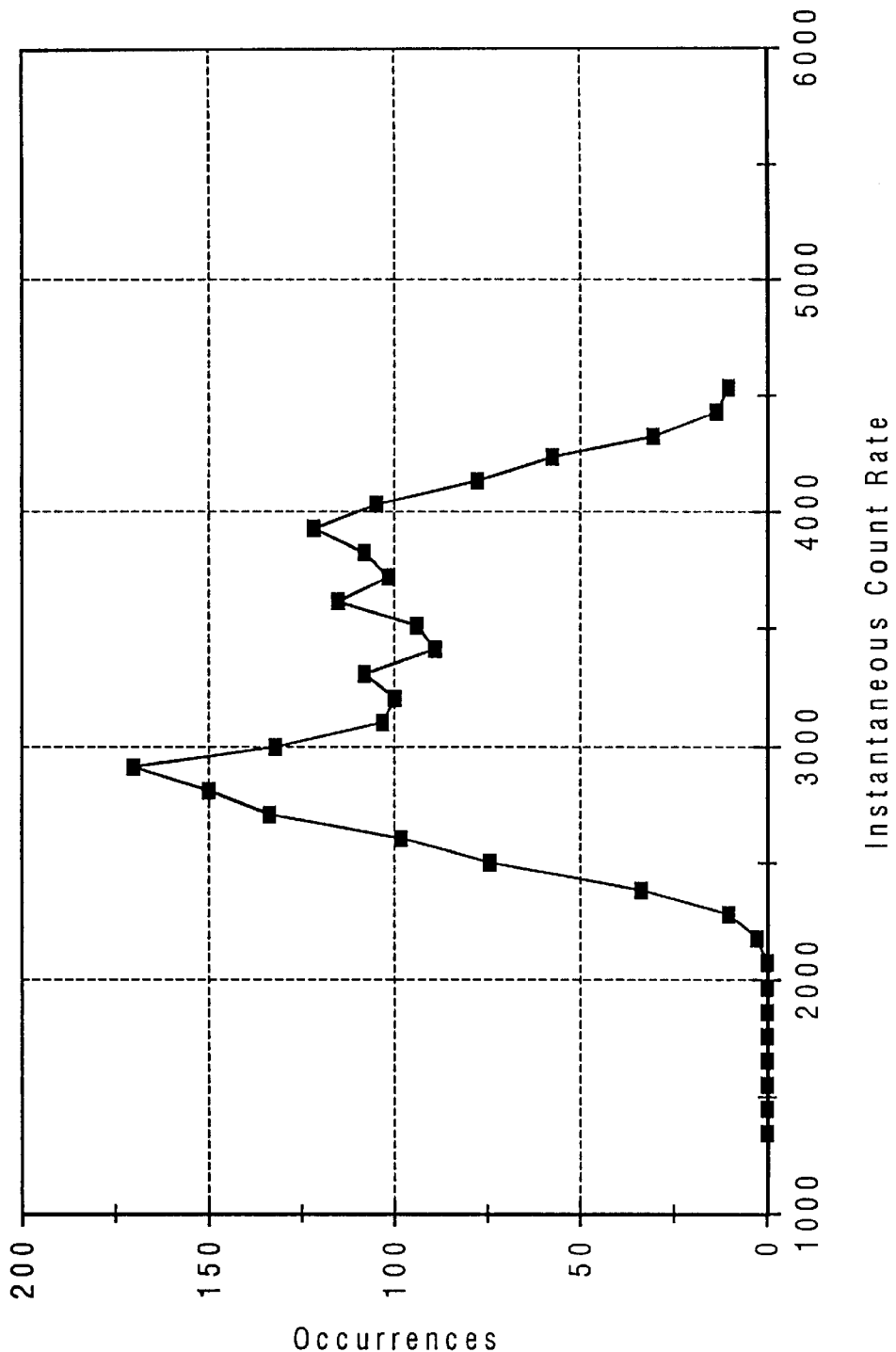
FIG. 7 is a histogram for high air and water flow rates at a vertical inclination.

FIG. 3 shows the density tool's counting histogram for single component water, while FIG. 4 shows a histogram for single component air. The x-axis of each figure shows the instantaneous count rate and the y-axis shows the number of occurrences of each count rate, within the sampling period (3 to 5 minutes). FIG. 5 shows a histogram acquired for a mixture at high water flow and low gas flow; the peak of the left (near-water peak) is much larger than the peak on the right (near-gas peak), and the two peaks are closer than the single component gas and water peaks are. FIG. 6 shows the reverse situation, a histogram for low water flow and high gas flow. Again, the peaks have moved toward one another, but now the near-air peak is higher. FIG. 7 shows a histogram for high air and water flow rates at a vertical inclination. Extreme turbulence and shearing has almost melded the two peaks into one, as little near-air or near-water mixture still exists.

By examining these histograms, it can be shown that the preferred sigma level generating the lowest errors in $Y_{h\_total}$ tends to change with the relative position of (distance between) the near-air and near-water peaks; however, determination of the peak positions becomes more difficult as they meld together at higher rates. To make this determination easier, the peaks can be "stripped" by removing the superposition of the two peaks that naturally occurs. The simplest way to do this is to assume that the truncated side of the higher peak is actually symmetrical about its centroid. The shape is accordingly reflected about the centroid, and subtracted from the raw (superposed) graph, which results in two well-defined and symmetrical peaks emerging. Determination of their positions is further facilitated by some averaging level being placed upon the histogram before stripping (10 level is exemplary).

A linear regression of the distance between the peaks can be used to select an acceptable sigma level. This regression is thus based on the value of $(C_l-C_h)/(C_a-C_w)$, referred to herein as the peak ratio, where $C_l$ is the count rate for the light phase (near-air) peak, $C_h$ is the count rate for the heavy phase (near-water) peak, $C_a$ is the calibration value of the air count rate and $C_w$ is the calibration value of the water count rate. The regression is preferably based on a large set of experimental data. Its validity does not depend upon prior knowledge of any well being interrogated, and uses as its input only information gleaned from the data itself.

This regression method for selecting an appropriate sigma level breaks down when only one peak is present, as with single component gas or water flow, since there is only one peak. Such situations can be automatically recognized, however, and the default value of 3σ is used.

Figure 8:
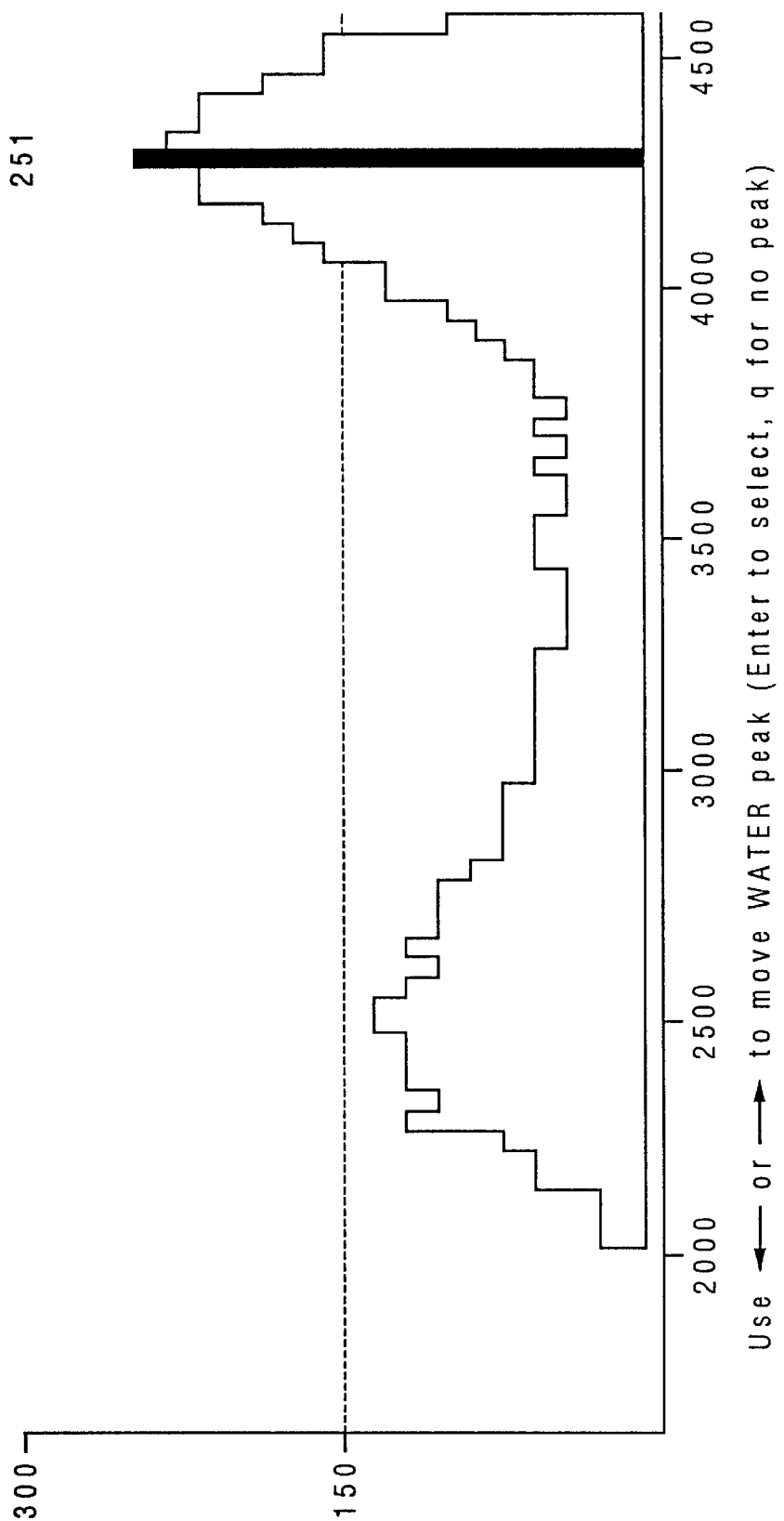
FIG. 8 is a histogram depicting optional interactive manipulation of sigma level selection used in the data reduction method of the present invention.

With appropriate software, the selection of the sigma level can be manipulated interactively, as shown in FIG. 8. The data depicted there are non-smoothed from a high air rate test. This utility (visual presentation of the histogram) can be generated during the data reduction process, and allow manual override of otherwise automatic peak selection. Especially at the difficult boundaries of low gas flow at near horizontal, this manual interaction is valuable in conjunction with the cross-section image. In the case where only one peak is recognized in the histogram, but the cross-section notes significant gas along the top of the flow pipe, the chance for maximum error arises, as the density tool may no longer intercept a representative sample to determine MHPD accurately. In this case, operator. judgment may be used to select an optimum sigma level.

Another correction should be applied in accounting for the fact that the larger hydrocarbon structures measured by fluid holdup tool 17 are actually displacing a quasi-continuous mixture that itself contains entrained hydrocarbons. In other words, the $Y_{h\_FPT}$ and $Y_{h\_FD}$ values are not simply added together to obtain $Y_{h\_total}$. Rather, the $Y_{h\_FPT}$ value is corrected before adding it to $Y_{h\_FD}$. Thus, the formula used for determining $Y_{h\_total}$ is $$Y_{h\_total} = Y_{h\_FD} + [Y_{h\_FPT} \times (1 - Y_{h\_FD})]$$

The present invention deviates from the popular prior art approach of characterizing the multi-component flow response of sensors in a flow loop, which can lead to problems since even minor differences in flow loop and field conditions can greatly affect the usefulness of correction charts. Instead, the data reduction method of the present invention avoids any dependence upon prior knowledge of well conditions, including inclination.

It may also be desirable to use histograms on the FPT sensory data, plotting the number of occurrences of contiguous hydrocarbon interval lengths. With a FPT sensor sample interval of 10 milliseconds (10 times faster than fluid density), hydrocarbon transients of less than 10 ms are seen as deflections of less than full scale, which is an artifact of the sampling speed. Some periods that indicate hydrocarbons may last for several contiguous 10 ms periods. A histogram of occurrences of duration pins in 10 ms intervals may be used to provide additional qualitative information related to the flow regime. At near horizontal inclinations with elongated bubble flow, contiguous hydrocarbon periods of several seconds may occur. A span of 500 (10 ms) bins may be useful to cover a range of hydrocarbon duration from 10 ms to five seconds.

Although the invention has been described with reference to specific embodiments, this description is not meant to be construed in a limiting sense. Various modifications of the disclosed embodiment, as well as alternative embodiments of the invention, will become apparent to persons skilled in the art upon reference to the description of the invention. For example, the invention could be used with different types of density tools, not just nuclear (or gamma—gamma) tools, including acoustic "Bendix type" resonant devices. Also, the invention is applicable to any measurements of fluid holdup in multiphase fluid flow, i.e., other than downhole, such as custody transfer of raw well product. It is therefore contemplated that such modifications can be made without departing from the spirit or scope of the present invention as defined in the appended claims.

We claim:

1. A method of determining a holdup value for a multiphase fluid, comprising the steps of:

calculating a first holdup component using a first detection technique which is insensitive to small inclusions of a first fluid constituent of the multiphase fluid dispersed in a second fluid constituent of the multiphase fluid;

calculating a second holdup component using a second detection technique which determines a percentage of the small inclusions of the first fluid constituent that are dispersed in the second fluid constituent; and combining the first and second holdup components to yield a total holdup value, wherein said combining step includes the step of compensating for an error in the first holdup component associated with displacement of the second fluid constituent by the small inclusions of the first fluid constituent.

2. The method of claim 1 wherein said step of calculating the first holdup component includes the step of measuring flow rates of the multiphase fluid.

3. The method of claim 1 wherein said step of calculating the second holdup component includes the step of measuring a density of the multiphase fluid.

4. The method of claim 3 wherein said step of calculating the second holdup component further includes the step of inferring a maximum heavy phase density (MHPD) of the multiphase fluid.

5. The method of claim 3 wherein the density measuring step includes the step of measuring attenuation of gamma rays passing through the multiphase fluid.

6. The method of claim 5 wherein:

said step of calculating the second holdup component further includes the step of inferring a maximum heavy phase density (MHPD) of the multiphase fluid; and said step of inferring the MHPD includes the step of identifying a lowest valid count rate of the gamma rays.

7. The method of claim 6 wherein said step of inferring the MHPD further includes the steps of:

identifying a heavy component count rate peak; and determining a center count rate for the MHPD by moving a selected number of standard deviations of the heavy component count rate peak upward from the lowest valid count rate.

8. The method of claim 7 wherein said step of inferring the MHPD further includes the step of selecting the number of standard deviations using a linear regression.

9. The method of claim 7 wherein said step of inferring the MHPD further includes the step of interactively selecting the number of standard deviations during density measurement.

10. The method of claim 1 wherein the multiphase fluid is flowing in a well borehole, and further comprising the step of lowering a tool string into the borehole, the tool string including means for acquiring data used to calculate the first and second holdup components.

11. The method of claim 1 wherein said combining step combines the first and second holdup components according to the equation $$Y_{h\_total} = Y_{h\_FD} + [Y_{h\_FPT} \times (1 - Y_{h\_FD})]$$

where $Y_{h\_total}$ is the total holdup value, $Y_{h\_FD}$ is the second holdup component, and $Y_{h\_FPT}$ is the first holdup component.

12. A device for measuring a holdup value for a multiphase fluid, comprising:

means for calculating a first holdup component using a first detection technique which is insensitive to small inclusions of a first fluid constituent of the multiphase fluid dispersed in a second fluid constituent of the multiphase fluid;

means for calculating a second holdup component using a second detection technique which determines a percentage of the small inclusions of the first fluid constituent that are dispersed in the second fluid constituent; and means for combining the first and second holdup components to yield a total holdup value, said combining means including means for compensating for an error in the first holdup component associated with displacement of the second fluid constituent by the small inclusions of the first fluid constituent.

13. The device of claim 12 wherein said means for calculating the first holdup component includes at least one flow sensor.

14. The device of claim 12 wherein said means for calculating the second holdup component includes means for measuring a density o f the multiphase fluid.

15. The device of claim 14 wherein said means for calculating the second holdup component further includes means for inferring a maximum heavy phase density (MHPD) of the multiphase fluid.

16. The device of claim 14 wherein said density measuring means further includes means for measuring attenuation of gamma rays passing through the multiphase fluid.

17. The device of claim 16 wherein said means for calculating the second holdup component further includes means for inferring a maximum heavy phase density (MHPD) of the multiphase fluid by identifying a lowest valid count rate of the gamma rays.

18. The device of claim 17 wherein said means for inferring the MHPD further includes means for identifying a heavy component count rate peak, and determining a center count rate for the MHPD by moving a selected number of standard deviations of the heavy component count rate peak upward from the lowest valid count rate.

19. The device of claim 18 wherein said means for inferring the MHPD further includes means for selecting the number of standard deviations using a linear regression.

20. The device of claim 18 wherein said means for inferring the MHPD further includes means for allowing interactive selection of the number of standard deviations during density measurement.

21. A production logging tool using the device of claim 12, and further comprising:
    a cable head;
    a fluid holdup tool having means for acquiring data used by said means for calculating the first holdup component; and
    a density tool having means for acquiring data used by said means for calculating the second holdup component, wherein said cable head, fluid holdup tool and density tool are adapted to be lowered into a well borehole.

22. The device of claim 12 wherein said combining means combines the first and second holdup components according to the equation $$Y_{h\_total}=Y_{h\_FD}+[Y_{h\_FPT}\times(1-Y_{h\_FD})]$$

where $Y_{h\_total}$ is the total holdup value, $Y_{h\_FD}$ is the second holdup component, and $Y_{h\_FPT}$ the first holdup component.

23. A production logging tool for measuring a holdup value for a multiphase fluid in a well borehole, comprising:
    a cable head;
    a fluid holdup tool, attached to said cable head, having means for acquiring first data, said fluid holdup tool being insensitive to small inclusions of a first fluid constituent of the multiphase fluid dispersed in a second fluid constituent of the multiphase fluid, and said means for acquiring the first data including at least one flow sensor;
    means for calculating a first holdup component based on the first data;
    a density tool, attached to said cable head, having means for acquiring second data, said density tool being sensitive to the small inclusions of the first fluid constituent that are dispersed in the second fluid constituent, and said means for acquiring the second data including at least one gamma ray detector;
    means for calculating a second holdup component based on the second data, including means for inferring a maximum heavy phase density (MHPD) of the multiphase fluid;
    means for combining the first and second holdup components to yield a total holdup value, according to the equation $$Y_{h\_total}=Y_{h\_FD}+[Y_{h\_FPT}\times(1-Y_{h\_FD})]$$

where $Y_{h\_total}$ is the total holdup value, $Y_{h\_FD}$ is the second holdup component, and $Y_{h\_FPT}$ is the first holdup component.

24. A method of inferring a maximum heavy phase density of a multiphase fluid, comprising the steps of:
    sampling the density of the multiphase fluid over brief sampling intervals using a density tool;
    generating a histogram of samples returned by said sampling step; and
    analyzing the histogram to establish a center of a heavy component peak.

25. The method of claim 24 wherein:
    the density tool measures different count rates of gamma rays; and
    the histogram is generated based on occurrences of the different count rates.

26. The method of claim 25 wherein said analyzing step includes the steps of:
    determining the standard deviation of the heavy component peak;
    identifying a lowest count rate in the histogram; and
    adding a number of standard deviations to the lowest count rate.

27. The method of claim 24 wherein said analyzing step includes the steps of:
    determining a standard deviation of the heavy component peak;
    identifying a low end of the heavy component peak; and
    adding a number of standard deviations to the low end of the heavy component peak.

28. The method of claim 24 further comprising the step of converting the center of the heavy component peak to a density value calibration.

* * * * *

UNITED STATES PATENT AND TRADEMARK OFFICE
CERTIFICATE OF CORRECTION

PATENT NO.    : 6,028,307
DATED         : February 22, 2000
INVENTOR(S)   : Allen R. Young, et al.

It is certified that error appears in the above-identified patent and that said Letters Patent is hereby corrected as shown below:

Column 7
Line 17, please delete "." after operator.

Column 9
Line 67, please insert --is-- in front of "the".

Column 10
Line 59, please delete "low end of the heavy component peak" and insert
--lowest count rate in the histogram--.

Signed and Sealed this

Nineteenth Day of June, 2001

*Attest:*

*Attesting Officer*

NICHOLAS P. GODICI
*Acting Director of the United States Patent and Trademark Office*